United States Patent [19]

Geiger

[11] 4,121,588
[45] Oct. 24, 1978

[54] DISPOSABLE HYPODERMIC SYRINGE AND METHOD OF MANUFACTURE

[75] Inventor: Kenneth E. Geiger, Palisades Park, N.J.

[73] Assignee: Becton, Dickinson and Company, Rutherford, N.J.

[21] Appl. No.: 797,069

[22] Filed: May 16, 1977

[51] Int. Cl.$^2$ .............................................. A61M 5/00
[52] U.S. Cl. ............................ 128/218 R; 128/218 N
[58] Field of Search ............... 128/218 R, 218 N, 234, 128/215, 221, 216

[56] References Cited

U.S. PATENT DOCUMENTS

| 3,306,291 | 2/1967 | Burke | 128/218 R |
| 3,320,954 | 5/1967 | Cowley | 128/218 N |

*Primary Examiner*—John D. Yasko
*Attorney, Agent, or Firm*—Kane, Dalsimer, Kane, Sullivan and Kurucz

[57] ABSTRACT

The disclosure is of a disposable hypodermic syringe and the method of its manufacture. The syringe comprises a barrel, a piston-plunger slidably mounted in the barrel, a handle and shank connected to the piston-plunger, a needle hub welded to and closing one end of the barrel and supporting a hypodermic needle, a shield for the needle and a cap which closes the other end of the barrel. A novel feature of the syringe of the invention is a weakened zone of the barrel in a line circumscribing the barrel at a point adjacent to the edge of the needle hub. An advantage of the syringe of the invention is its disposability after use. To dispose of the syringe, the operator first replaces the shield over the needle and hub. The hub with the enclosed needle may then be broken off along the weakened zone of the barrel by bending, so that the barrel is destroyed and the needle is enclosed within the shield and hub in such a manner that it may not be re-used or misused without considerable and extraordinary effort. The needle hub and barrel form a sealed annular chamber when assembled, which isolates the barrel-hub welding zone from the fluid path of the syringe. This chamber will trap any flash which may be generated by the welding process.

3 Claims, 12 Drawing Figures

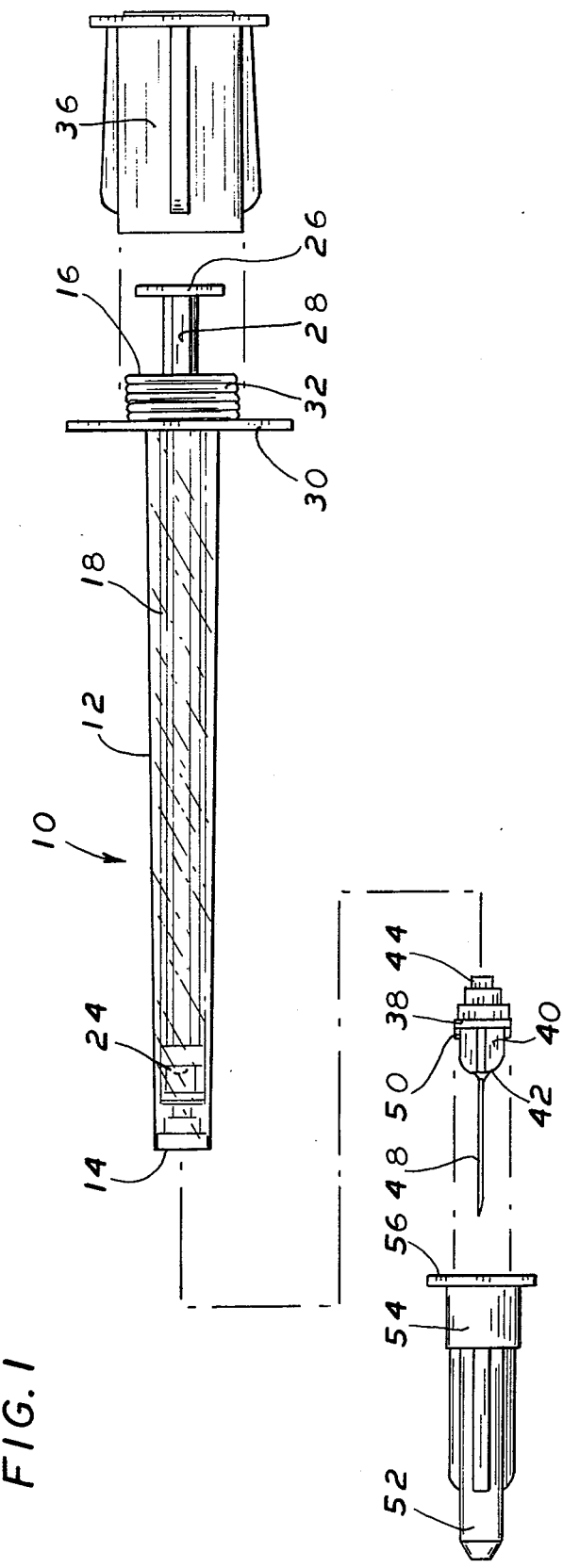
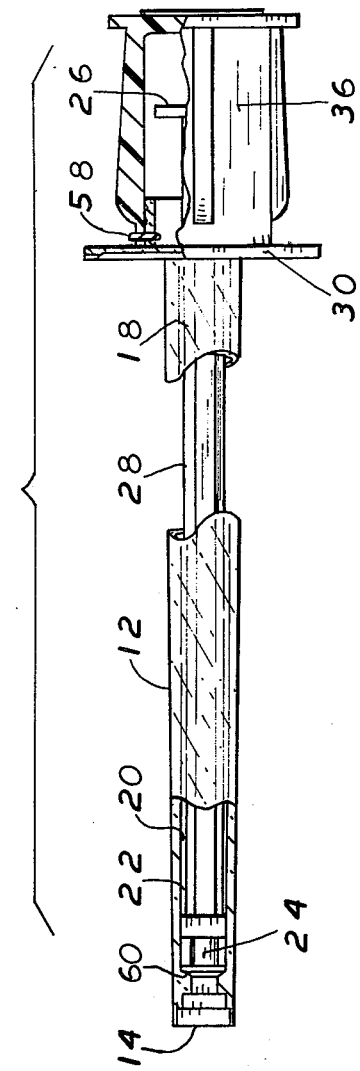

4,121,588

DISPOSABLE HYPODERMIC SYRINGE AND METHOD OF MANUFACTURE

BACKGROUND OF THE INVENTION

1. Field of the Invention

The invention is related to hypodermic syringes and more particularly relates to disposable hypodermic syringes and the method of their manufacture.

2. Brief Description of the Prior Art

Hypodermic syringes are well known articles and the literature is replete with their descriptions. Prior hereto, after one completed the single use of the prior art hypodermic syringe and wished to dispose of it, he had to resort to a separate device to sever the needle and barrel components of the syringe to assure that they were destroyed beyond use; see for example U.S. Pat. Nos. 3,404,593; 3,444,620; 3,469,750; 3,585,835; 3,736,824; and 3,914,865.

The present invention obviates the need for such devices since the hypodermic syringe of the present invention may be readily destroyed after use without the need for separate devices.

SUMMARY OF THE INVENTION

The invention comprises a disposable, hypodermic syringe, which comprises; a syringe barrel having inner and outer surfaces and open first and second ends; a piston-plunger slidably mounted in said barrel and forming a seal with the inner surface of said barrel; a handle; a shank connecting said handle to said piston-plunger and extending with the handle out of said first end of said barrel; a removable cap attached to said first end of said barrel, in a protective position over the handle, extending shank and open first end; a hub which comprises a central body portion, first and second ends and a bore through said body communicating between the first and second ends of said hub, said hub being mounted in the second open end of said barrel so as to partially close that end with the first end of said hub; a hypodermic needle mounted in the bore of said hub with the cutting end thereof extended distally from the second end of said hub, the bore of said needle being in open communication with the bore of said barrel; a removable needle shield mounted on the second end of said hub in a protective position over said needle, said shield having a skirt extending over and removably fixed to the outer surface of the second end of said barrel; and a weakened zone of said barrel, in a line circumscribing said barrel adjacent to the edge of said hub.

The invention also comprises a method of assembly for disposable, thermoplastic, hypodermic syringes. The method comprises; providing a thermoplastic syringe barrel having inner and outer surfaces and open first and second ends; providing a thermoplastic needle hub which comprises a central body portion, first and second ends and a bore through said body, communicating between the first and second ends of said hub; providing a thermoplastic needle shield, said shield having a skirt portion; mounting said hub inside said shield so that said skirt is extending over said hub, forming an annular space between a portion of said hub and said skirt, said space being adapted to receive the second end of said barrel in frictional engagement between said hub and said skirt; frictionally engaging the second end of said barrel in said space; and spin welding the second end of said barrel to said hub and shield.

The advantage of the method of the invention is a lowered cost of assembly, shorter time requirements for assembly and lower standards of dimensional specifications for the parts to be assembled. This method also provides inherent built-in destructability as desired for a disposable syringe.

The term "disposable hypodermic syringe" as used throughout the specification and claims means a syringe which after use may be destructed and safely disposed of in a manner whereby it may not be reusable.

The term "weakened zone" as used herein means a zone which is relatively weak in comparison to adjacent zones so that when a bending pressure or moment is exerted at or near the weakened zone, it will readily fracture at that zone, relieving pressure on the adjacent zones.

BRIEF DESCRIPTION OF THE DRAWINGS

FIG. 1 is an isometric view of an embodiment hypodermic syringe of the invention shown in disassembly.

FIG. 2 is a cross-section in part of the partially assembled syringe shown in FIG. 1.

DETAILED DESCRIPTION OF THE PREFERRED EMBODIMENTS OF THE INVENTION

Figure 3:
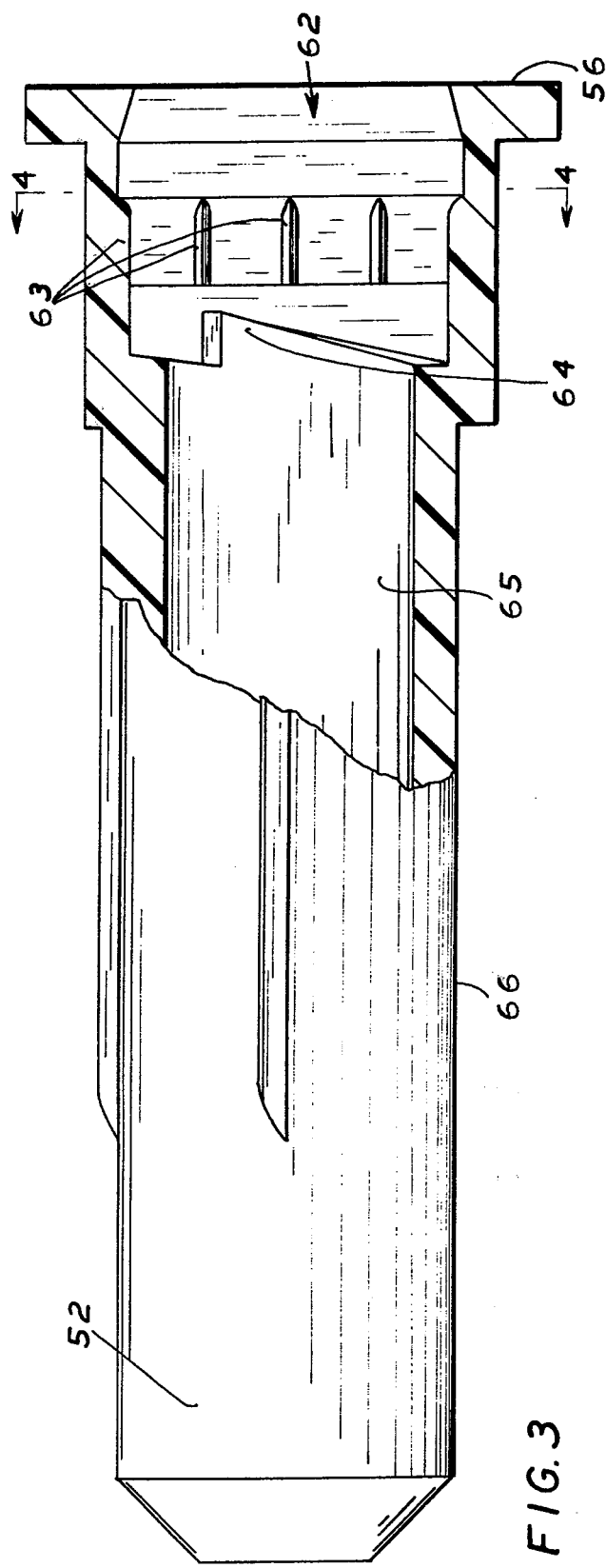
FIG. 3 is an enlarged cross-section in part, side views of the shield component of the syringe shown in FIG. 1.

Referring first to FIG. 1, an isometric view of the disassembled preferred embodiment syringe 10, one may see the basic components thereof. Thus, syringe 10 comprises a thermoplastic syringe barrel 12 having an open first end 14 and an open second end 16. The syringe 10 also has an outer barrel surface 18 and an inner barrel surface 20 (see FIG. 2). A bore 22 (not seen in FIG. 1) traverses the body of barrel 12 from end 14 to end 16 providing communication between ends 14, 16. An elastomeric piston-plunger 24 is slidably mounted in the barrel bore 22 and forms a sliding seal with the inner surface 20 of said barrel 21 (see FIG. 2). The syringe assembly 10 also includes a handle 26 to facilitate grasping a shank 28 which connects the handle 26 to sliding piston-plunger 24. Shank 28 with attached handle 26 facilitates movement of the elastomeric piston-plunger 24 forward towards end 14 and backward towards end 16 of the barrel 12. The handle 26 and a portion of shank 28 extend outwardly from the bore 22 of barrel 12 through the open end 16. The end 16 of barrel 12 also has attached thereto a finger grasping flange 30 to facilitate operation of the syringe 10. Ribs 32 circumscribe end 16 of barrel 12 to facilitate the frictional mounting of a removable cover or cap 36. Cap 36 functions as a protective cover over the handle 26, extended (out of opening 16) portion of shank 28 and the open end 16 of barrel 12.

Figure 8:
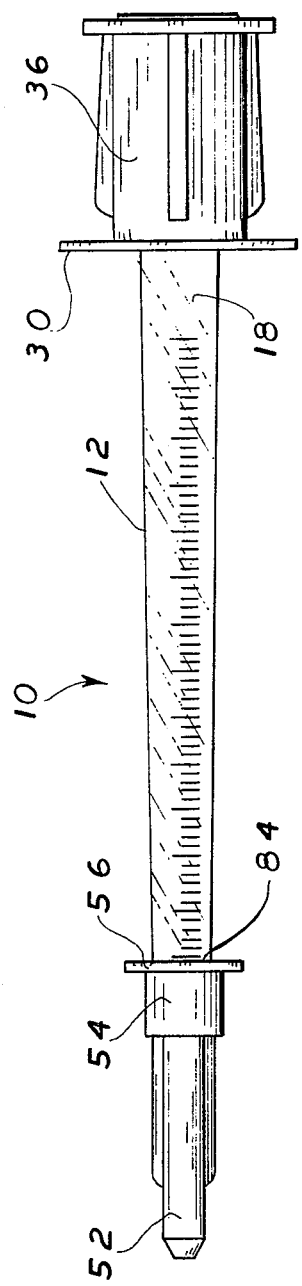
FIG. 8 is an isometric view of the assembled components of the syringe shown in FIG. 1.

Referring to FIG. 2, one can see the assembled removable cap 36 and its seating between ribs 32 and lugs 34 in a frictional fit. In a preferred embodiment, the removable cap 36 may be secured by a heat stake 58 to the end 16 of barrel 12. One can then be alerted if cap 36 has been previously removed or tampered with, thereby possibly contaminating the sterility of the syringe 10. Heat stake 58 may be a simple heat sealing of the parts in a very small area, the area being easily severed by rotation of cap 36 on end 16. The FIG. 2 also shows the traversal of bore 22 by shank 28. As also shown, the piston-plunger 24 is stopped from complete traversal of bore 22 by seal ring 60 just inward of open end 14. Seal ring 60 is integral with and annularly disposed about the inner surface 20 of barrel 12. Referring again to FIG. 1, one may see the thermoplastic needle mounting hub 38 having a central body portion 40 and ends 42, 44. Traversing the body of hub 38 from end 42 to end 44 is a bore communicating between the ends 42, 44 (bore not seen in FIG. 1). Mounted in the bore of hub 38 is a hypodermic needle 48 having its sharpened or cutting end distal to the end 42 of hub 38. The bore of the needle 48 is in open communication with the bore of the hub 38 and with bore 22 of barrel 12 when the hub 38 is mounted thereon. The hub 38 is adapted to mate with and be mounted within the open end 14 of barrel 12 as will be described in greater detail hereinafter. The hub 38 is also adapted to be inserted into end 56 of thermoplastic needle shield 52, said needle shield 52 having a skirt portion 54 and an open end 56 for receiving the hub 38 with mounted needle 48. Referring to FIG. 8, one may observe an isometric view of the assembled hypodermic syringe 10 of the invention.

Figure 5:
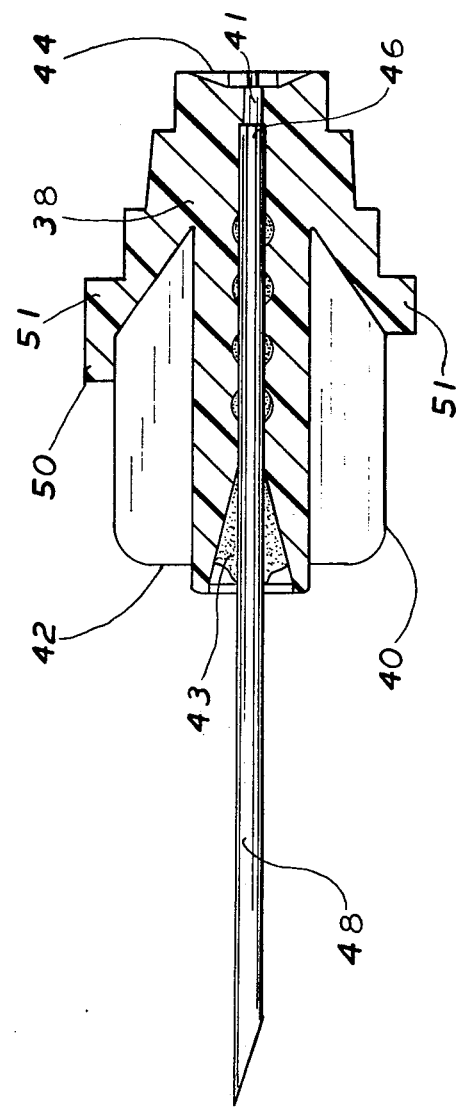
FIG. 5 is an enlarged cross-sectional, side view of the needle mounting hub component of the syringe shown in FIG. 1.
Figure 4:
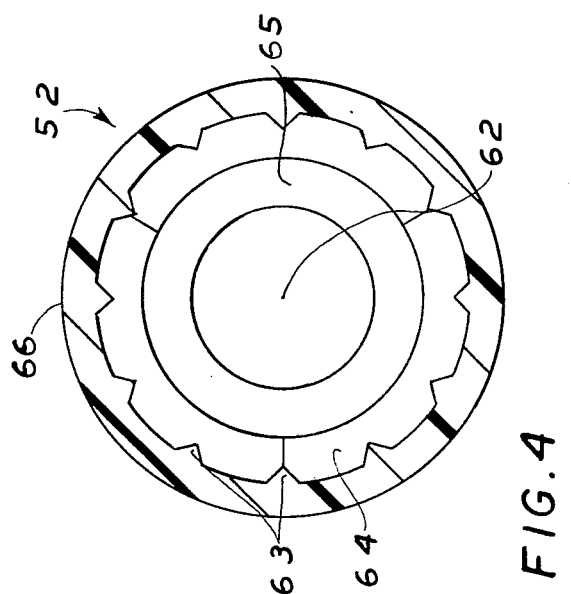
FIG. 4 is a view along lines 4—4 of FIG. 3.
Figure 6:
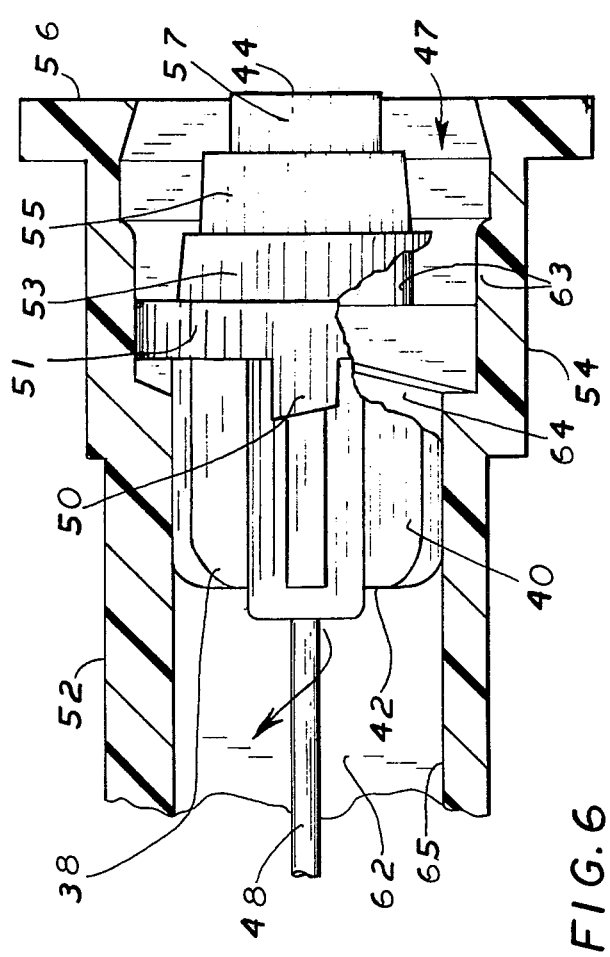
FIG. 6 is an enlarged cross-sectional side view of a fragment of the shield component shown in FIG. 3 with the needle hub of FIG. 5 being inserted therein.

FIG. 3 is a cross-section in part of the thermoplastic needle shield 52 and shows blind bore 62 having a single access opening at end 56. Ribs 63 are provided on the inner walls 65 of shield 52 and function to frictionally engage hub 38 and to provide a light weld between the shield 52 and the barrel 12 as will be described hereinafter. A cam surface 64 is also provided on the inner walls 65 of shield 52, ribs 63 and cam 64 being located adjacent to end 56. Details of the inner structure of needle shield 52 may be observed by referring now to FIG. 4, a view along lines 4—4 of FIG. 3. Thus, the shield 52 is made up of an outer wall 66, inner wall 65, annularly disposed internal ribs 63, camming surface 64 and an internal blind bore 62 closed at one end and open at end 56. FIG. 5 is an enlarged cross-sectional in part side elevation of hub 38 and shows that central body 40 is traversed by a bore 41 which serves to receive and mount needle 48. Adhesive 43 such as an epoxy adhesive serves to firmly mount needle 48 in the bore 41. The end 46 of needle 48 is continuous with and in axial alignment with the bore 41 so that the bore of needle 48 and bore 41 are continuous and axially aligned with each other. A flange 51 of hub 38 is radially disposed from body 40 and is adapted to form an interference fit with the ribs 63 of shield 52. Extending forward of flange 51 is a lug 50 which forms a lock with cam 64 on the inner walls 65 of shield 52 when the shield 52 is rotated about the body of hub 38. Further details of the mounting of hub 38 in shield 52 may be observed by referring now to FIG. 6, a cross-sectional, enlarged view of hub 38 being inserted and mounted within the open end 56 of shield 52. Thus, it may be seen that hub 38 is rotatably moved into bore 62. As the hub 38 is moved inward in blind bore 62 by rotation, locking lug 50 engages cam 64 to stop rotation and forward movement of hub 38 in bore 62. The hub 38 is then nested within bore 62 and stopped from rotating therein in one direction. It will also be observed that hub 38 nests completely within bore 62 (see FIG. 7) the hub end 42 being in contact with the inner walls 65. Hub end 44 however is free of contact with the inner walls 65, leaving a space 47 between hub 38 and the skirt portion 54 of shield 52. Space 47 is adapted to receive end 14 of barrel 12 as will be seen in FIG. 7.

Figure 7:
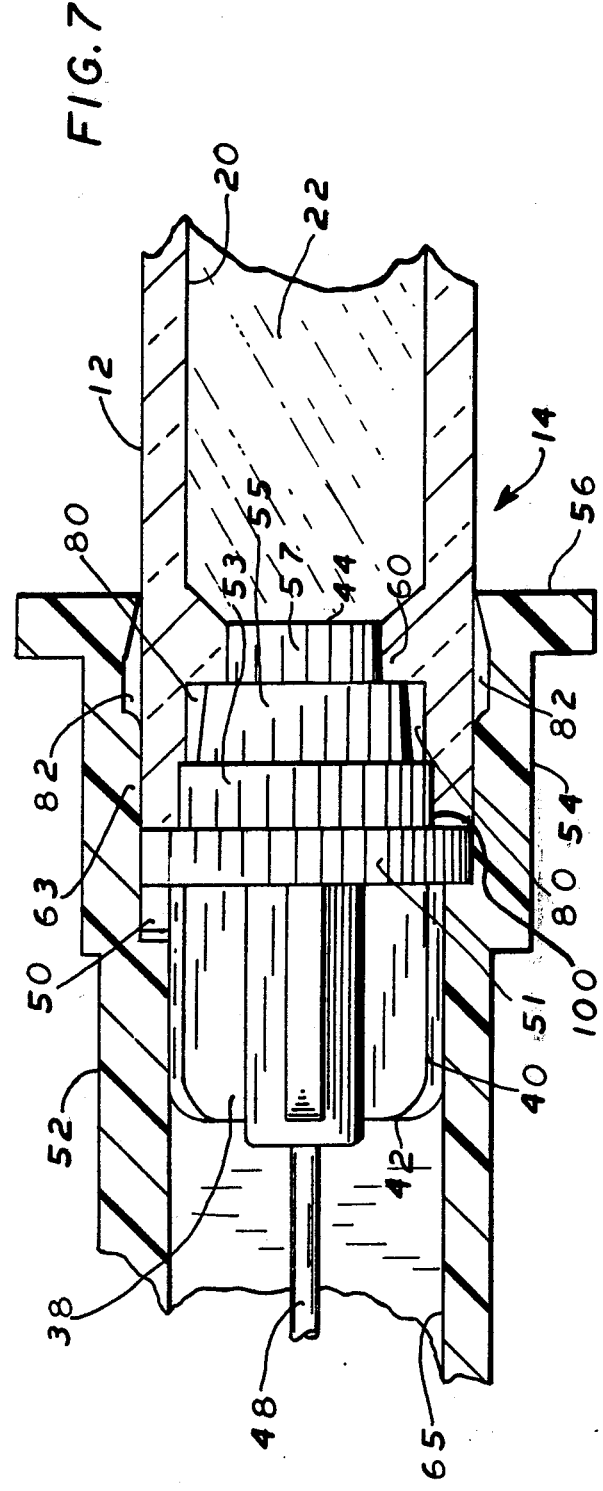
FIG. 7 is an enlarged cross-sectional side elevation as seen in FIG. 6 but with the barrel component of the syringe being initially mounted to the hub.
Figure 9:
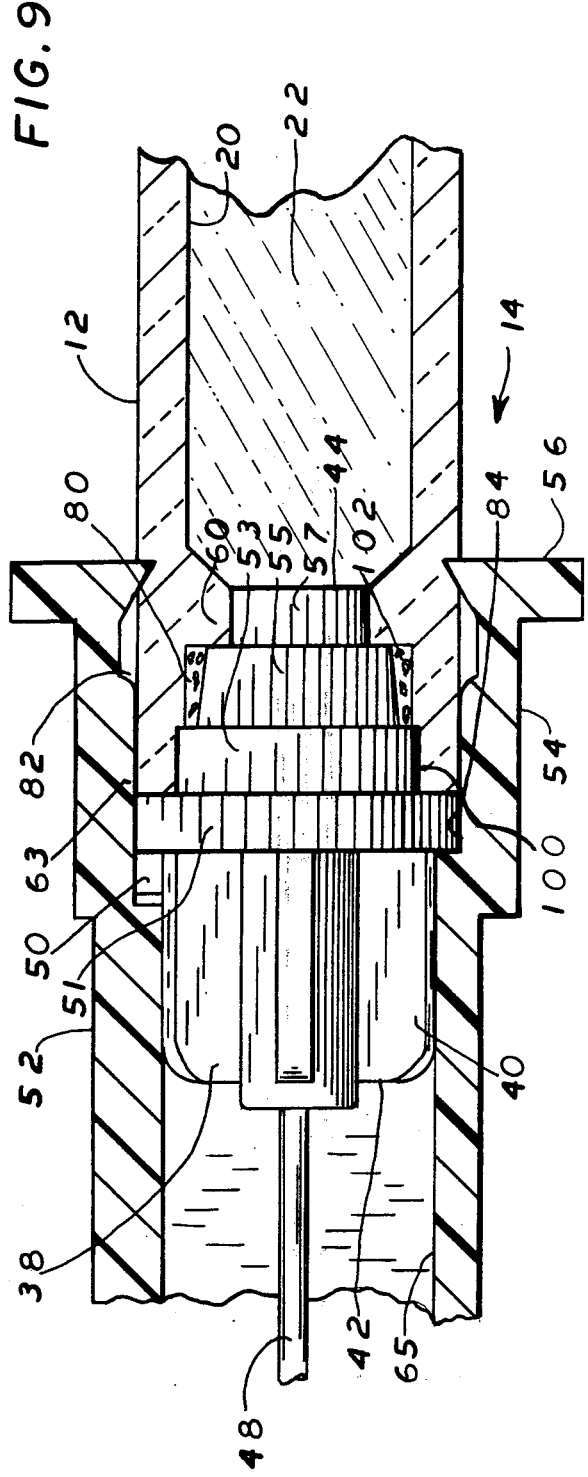
FIG. 9 is a view as shown in FIG. 7 but following completion of the assembly.

To assemble the component parts of syringe 10, the thermoplastic hub 38 is first provided with needle 48 mounted therein. Thermoplastic shield 52 is then secured to hub 38 as described above and the assembled shield 52 — hub 38 mounted in the open end 14 of barrel 12 by insertion to provide a frictional engagement, as shown in FIG. 8. Details of the engagement may be seen in FIG. 7, an enlarged, cross-sectional view of that fragment of assembled syringe 10 seen in FIG. 8, wherein the hub 38 is mounted in the end 14 of barrel 12, so as to partially close that end 14 with the end 44 of hub 38. As seen in FIG. 7, an annular recess is cut into the body portion 40 of hub 38 to form step 53 which mates with and engages in a frictional fit with a recess 100 cut into the inner surface 20 of barrel 12. Adjacent to step 53 is a deeper annular recess 55 cut on a bias to form a wall of chamber 80. Annular chamber 80 is formed between recess 55 of hub 38 and the inside wall 20 of barrel 12. Another annular chamber 82 is formed between the shield 52 skirt 54 at the termination of ribs 63 and the outer surface 18 of barrel 12 at a point adjacent to the end 56. Chamber 82 may be in fact an annular recess in the inner wall 65 of shield 52 at open end 56. Adjacent to step 53 is another step 57 formed by recessing the body 40 of hub 38 right at end 44. This step 57 is adapted to mate and seal with seal ring 60 which is an annular seal ring formed integrally on inner surface 20 of barrel 12. With the hub 38 and shield 52 inserted in the open end of barrel 12 as shown in FIG. 7, the preferred method of assembly may be carried out, i.e.; spin welding of hub 38 and shield 52 to barrel 12. Thus, after initial insertion into the open end 14 of barrel 12, barrel 12 is held stationary while the assembled hub 38 and shield 52 are spun very rapidly under axial pressure for a controlled interval. The locking of hub 38 by lug 50 engaging cam surface 64 holds these two components stationary during the spin welding procedure. Frictional heat between the end 14 of barrel 12 and the hub 38 during spinning cause a welding of the thermoplastic between step 53 and recess 100, among other points. This secures and fuses hub 38 to barrel 12. At the same time, ribs 63 of shield 52 fuse with the outer surface 18 of barrel 12 to provide a light weld, which is breakable, between shield 52 and barrel 12. This provides a tamper-proof indicator to alert one if the sterility of the assembly 10 has been broken and to seal the shield 52. Referring to FIG. 9, one can see the union between hub 38, shield 52 and barrel 12 after spin welding. During the spin welding process, pieces of flashing 102 may be freed from the surface of hub 38 and/or the inner walls 20 of barrel 12. These flashings are trapped in annular chambers 80 so that they are not forced onward and into the interior of bore 22 of the syringe barrel 12. This obviates the need to flush the bore 22 after spin-welding. Also, the spin welding creates a zone of weakness circumscribing barrel 12 at a point 84 adjacent to the end 14 of barrel 12 at the mating surfaces of the barrel 12 and the hub 38, which have now been welded together. This "weak zone" is due to molecular orientation which occurs within the weld itself. This weld is sufficiently strong to withstand an axial force or a shearing force. However, the zone 84 will separate when bent and "peeled" as will be described hereinafter.

The piston-plunger 24 attached to shank 28 may now be inserted into barrel 12 and end 16 covered attachment of cap 36 and the heat stake 58 produced.

Figure 10:
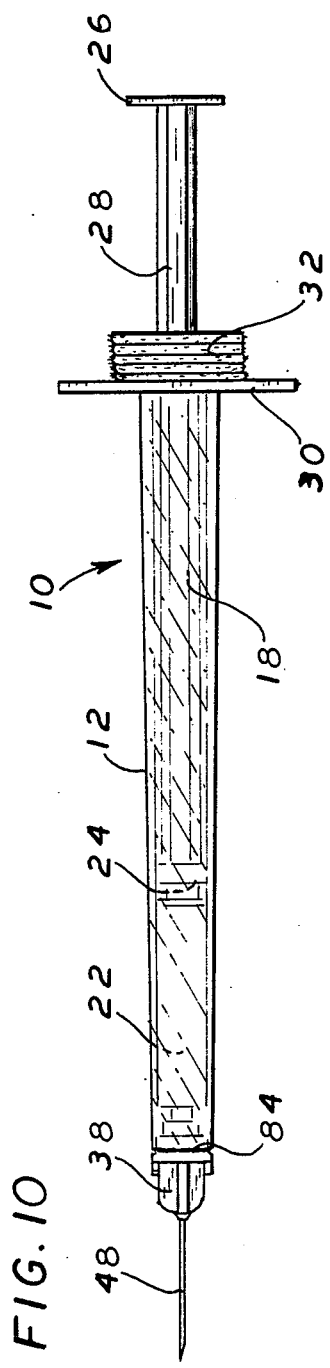
FIG. 10 is a view of the embodiment syringe seen in FIG. 8 but with the plunger shield removed.
Figure 11:
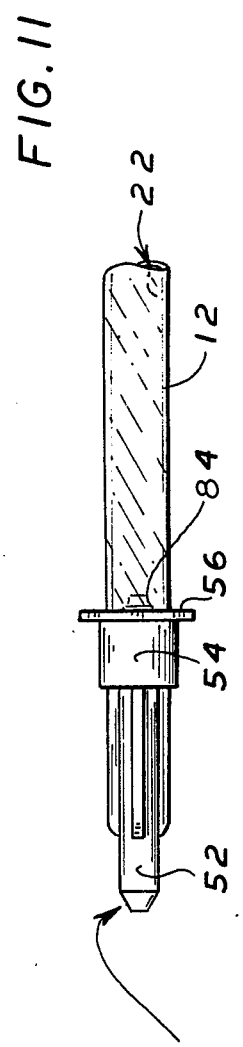
FIG. 11 is an isometric view of the enclosed needle end of the syringe embodiment shown in FIG. 8.
Figure 12:
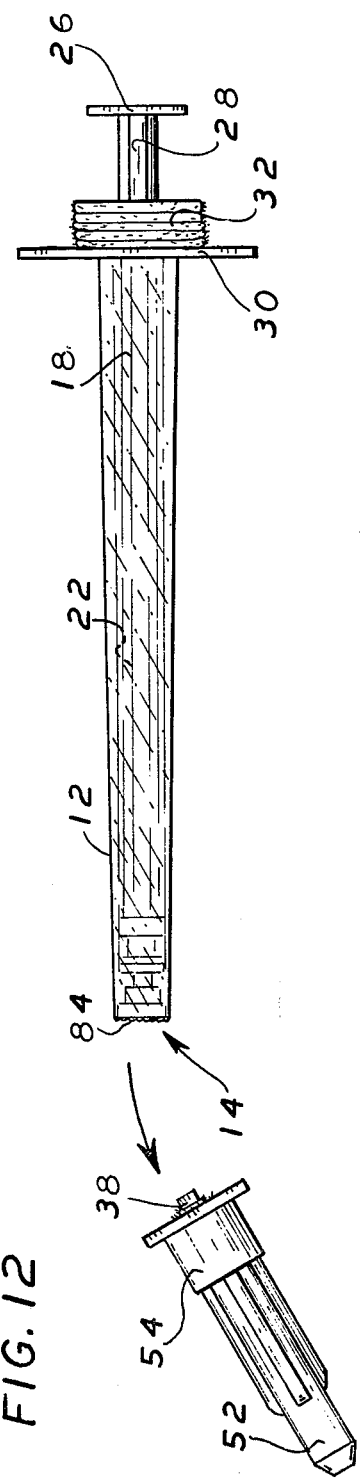
FIG. 12 is an isometric view of the disposable syringe embodiment of FIG. 8, shown after destruction.

The syringe 10 may be used in a conventional manner, by first removing shield 52 and cap 36 as shown in FIG. 10. Following use, the syringe is disposed of by first replacing shield 52. The shield 52 is rotated back onto the hub 38 and barrel 12 as shown in FIG. 11, a fragmentary enlarged view of the end 14 of barrel 12. With the shield 52 mounted again on hub 38 and barrel 12, one may quickly bend the shield 52 out of axial alignment with barrel 12. This will sever the thermoplastic barrel 12 at the weakened zone 84 as is shown in FIG. 12. The result is a breaking of barrel 12 so that the syringe barrel 12 may not be used again. The needle 48 and hub 38 are enclosed in the needle shield 52, secured by friction, and can only be removed by destruction of shield 52. The needle 48 being so enclosed, may be safely disposed of. There is a complete destruction of the future usability of hypodermic syringe 10.

The syringe 10 may be fabricated of conventional materials, conventionally employed in the manufacture of such articles. Preferably, the barrel 12, hub 38 and shield 52 are made of thermoplastics such as polypropylene and like synthetic polymeric resins.

The piston-plunger 24 is preferably fabricated from an elastomer such as natural or synthetic rubbers.

Spin welding techniques and apparatus are so well known in the art that a lengthy discussion is not warranted herein.

Those skilled in the art will appreciate that many modifications may be made to the above-described preferred embodiments without departing from the scope and spirit of the invention. The assembled syringe 10 may be sterilized by gamma radiation and like techniques.

What is claimed:

1. A disposable, hypodermic syringe, which comprises:
    a syringe barrel having inner and outer surfaces and open first and second ends;
    a piston-plunger slidably mounted in said barrel and forming a seal with the inner surface of said barrel;
    a handle;
    a shank connecting said handle to said piston-plunger and extending with the handle out of said first end of said barrel;
    a removable cap attached to said first end of said barrel, in a protective position over the handle, extending shank and open first end;
    a hub which comprises a central body portion, first and second ends and a bore through said body communicating between the first and second ends of said hub, said hub being spin welded to the second open end of said barrel so as to partially close that end with the first end of said hub at a welding zone formed at the mating surfaces of the barrel and the hub;
    a hypodermic needle mounted and firmly adhered in the bore of said hub with the cutting end thereof extended distally from the second end of said hub, the bore of said needle being in open communication with the bore of said barrel;
    a removable needle shield mounted on the second end of said hub in a protective position over said needle, said shield having a skirt extending over and removably fixed to the outer surface of the second end of said barrel; and
    a weakened zone of said barrel, in a line circumscribing said barrel at the junction of said barrel and said hub.

2. The syringe of claim 1 wherein said barrel, hub and shield are fabricated from thermoplastic polymeric resins.

3. The syringe of claim 1 wherein there is an annular chamber between a portion of said hub and the inner surface of said barrel which isolates the welding zone from the fluid path of the syringe and which will trap any flash generated by the weld.

* * * * *